US012391968B2

(12) United States Patent
Ogawa et al.

(10) Patent No.: US 12,391,968 B2
(45) Date of Patent: Aug. 19, 2025

(54) PRODUCTION METHOD FOR RARE FATTY ACID USING NOVEL ENZYME, AND NOVEL RARE FATTY ACID

(71) Applicant: NOSTER INC., Muko (JP)

(72) Inventors: Jun Ogawa, Kyoto (JP); Shigenobu Kishino, Kyoto (JP); Kohey Kitao, Kyoto (JP)

(73) Assignee: NOSTER INC., Muko (JP)

( * ) Notice: Subject to any disclaimer, the term of this patent is extended or adjusted under 35 U.S.C. 154(b) by 956 days.

(21) Appl. No.: 17/599,847

(22) PCT Filed: Mar. 27, 2020

(86) PCT No.: PCT/JP2020/013983
§ 371 (c)(1),
(2) Date: Sep. 29, 2021

(87) PCT Pub. No.: WO2020/203751
PCT Pub. Date: Oct. 8, 2020

(65) Prior Publication Data
US 2022/0042053 A1 Feb. 10, 2022

(30) Foreign Application Priority Data

Mar. 29, 2019 (JP) ................................. 2019-067966

(51) Int. Cl.
*C12P 7/6427* (2022.01)
*C07C 59/42* (2006.01)
*C12N 9/88* (2006.01)
*C12N 15/70* (2006.01)

(52) U.S. Cl.
CPC ............ *C12P 7/6427* (2013.01); *C07C 59/42* (2013.01); *C12N 9/88* (2013.01); *C12N 15/70* (2013.01)

(58) Field of Classification Search
CPC .............................. C12P 7/6432; C07C 59/42
USPC ......................................................... 514/560
See application file for complete search history.

(56) References Cited

U.S. PATENT DOCUMENTS

| | | |
|---|---|---|
| 2015/0125911 A1 | 5/2015 | Ogawa et al. |
| 2015/0342916 A1 | 12/2015 | Ogawa et al. |
| 2016/0000739 A1 | 1/2016 | Ogawa et al. |
| 2017/0000752 A1 | 1/2017 | Ogawa et al. |

(Continued)

FOREIGN PATENT DOCUMENTS

| | | |
|---|---|---|
| JP | 2007-252333 A | 10/2007 |
| JP | 2007-259712 A | 10/2007 |

(Continued)

OTHER PUBLICATIONS

Oleate hydratase [*Clostridium* sp.]—NCBI Reference Sequence WP_300347940.1, NCBI, deposited 1994. (Year: 1994).*

(Continued)

*Primary Examiner* — Jeffrey S Lundgren
*Assistant Examiner* — Heather Dahlin
(74) *Attorney, Agent, or Firm* — Leydig, Voit & Mayer, Ltd.

(57) ABSTRACT

A method for producing a hydroxylated fatty acid by a hydration reaction using a novel enzyme derived from the genus *Clostridium* in the soil and using fatty acid as a substrate is provided by the present invention. In addition, a novel rare fatty acid with utility value which is obtained by the production method is also provided.

9 Claims, 1 Drawing Sheet
Specification includes a Sequence Listing.

(56) References Cited

U.S. PATENT DOCUMENTS

| | | | |
|---|---|---|---|
| 2017/0007564 A1 | 1/2017 | Ogawa et al. | |
| 2017/0022526 A1 | 1/2017 | Ogawa et al. | |

FOREIGN PATENT DOCUMENTS

| | | | |
|---|---|---|---|
| JP | 2011-184411 A | 9/2011 |
| WO | WO 2013/168310 A1 | 11/2013 |
| WO | WO 2014/069227 A1 | 5/2014 |
| WO | WO 2014/129384 A1 | 8/2014 |
| WO | 2015/111701 A1 | 7/2015 |
| WO | WO 2015/111699 A1 | 7/2015 |
| WO | WO 2015/111700 A1 | 7/2015 |

OTHER PUBLICATIONS

Yoshimoto T, Takahashi Y. Arachidonate 12-lipoxygenases. Prostaglandins & other lipid mediators. Aug. 1, 2002;68:245-62. (Year: 2002).*

Careaga MM, Sprecher H. Synthesis of two hydroxy fatty acids from 7, 10, 13, 16, 19-docosapentaenoic acid by human platelets. Journal of Biological Chemistry. Dec. 10, 1984;259(23):14413-7. (Year: 1984).*

Kühn H, Schewe T, Rapoport SM. The stereochemistry of the reactions of lipoxygenases and their metabolites. Proposed nomenclature of lipoxygenases and related enzymes. Advances in Enzymology and Related Areas of Molecular Biology. Jan. 1, 1986;58:273-311. (Year: 1986).*

Prem S, Helmer CP, Dimos N, Himpich S, Bruck T, Garbe D, Loll B. Towards an understanding of oleate hydratases and their application in industrial processes. Microbial Cell Factories. Apr. 9, 2022;21(1):58. (Year: 2022).*

Careaga MM, Sprecher H. Metabolism of 8, 11, 14, 17-eicosatetraenoic acid by human platelet lipoxygenase and cyclooxygenase. Biochimica et Biophysica Acta (BBA)-Lipids and Lipid Metabolism. Jul. 13, 1987;920(1):94-101. (Year: 1987).*

Hagedoorn PL, Hollmann F, Hanefeld U. Novel oleate hydratases and potential biotechnological applications. Applied Microbiology and Biotechnology. Aug. 2021;105:6159-72. (Year: 2021).*

Ha et al., "Anticarcinogens from fried ground beef: heat-altered derivatives of linoleic acid," *Carcinogenesis*, 8(12): 1881-1887 (1987).

Ip et al., "Mammary Cancer Prevention by Conjugated Dienoic Derivative of Linoleic Acid," *Cancer Res.*, 51(22): 6118-6124 (1991).

Kim et al., "9-oxo-10(E), 12(E)-octadecadienoic acid derived from tomato is a potent PPAR a agonist to decrease triglyceride accumulation in mouse primary hepatocytes," *Mol. Nutr. Food Res.*, 55(4): 585-593 (2011).

Kim et al., "Potent PPARa Activator Derived from Tomato Juice, 13-oxo-9,11-Octadecadienoic Acid, Decreases Plasma and Hepatic Triglyceride in Obese Diabetic Mice," *PLoS One*, 7(2): e31317 (2012).

Kishino, "Lipid Metabolisms of Intestinal Bacteria and Physiological Functions on Fatty Acid Metabolites," *Shokuhin to Kaihatsu (Food Processing and Ingredients)*, 54: 1855-1863 (2019).

Lee et al., "Conjugated linoleic acid and atherosclerosis in rabbits," *Atherosclerosis*, 108(1): 19-25 (1994).

Sakurama et al., "Biohydrogenation of $C_{20}$ polyunsaturated fatty acids by anaerobic bacteria," *J. Lipid Res.*, 55(9): 1855-1863 (2014).

Japanese Patent Office, International Search Report in International Patent Application No. PCT/JP2020/013983 (Apr. 28, 2020).

Japanese Patent Office, Written Opinion of the International Searching Authority in International Patent Application No. PCT/JP2020/013983 (Apr. 28, 2020).

\* cited by examiner

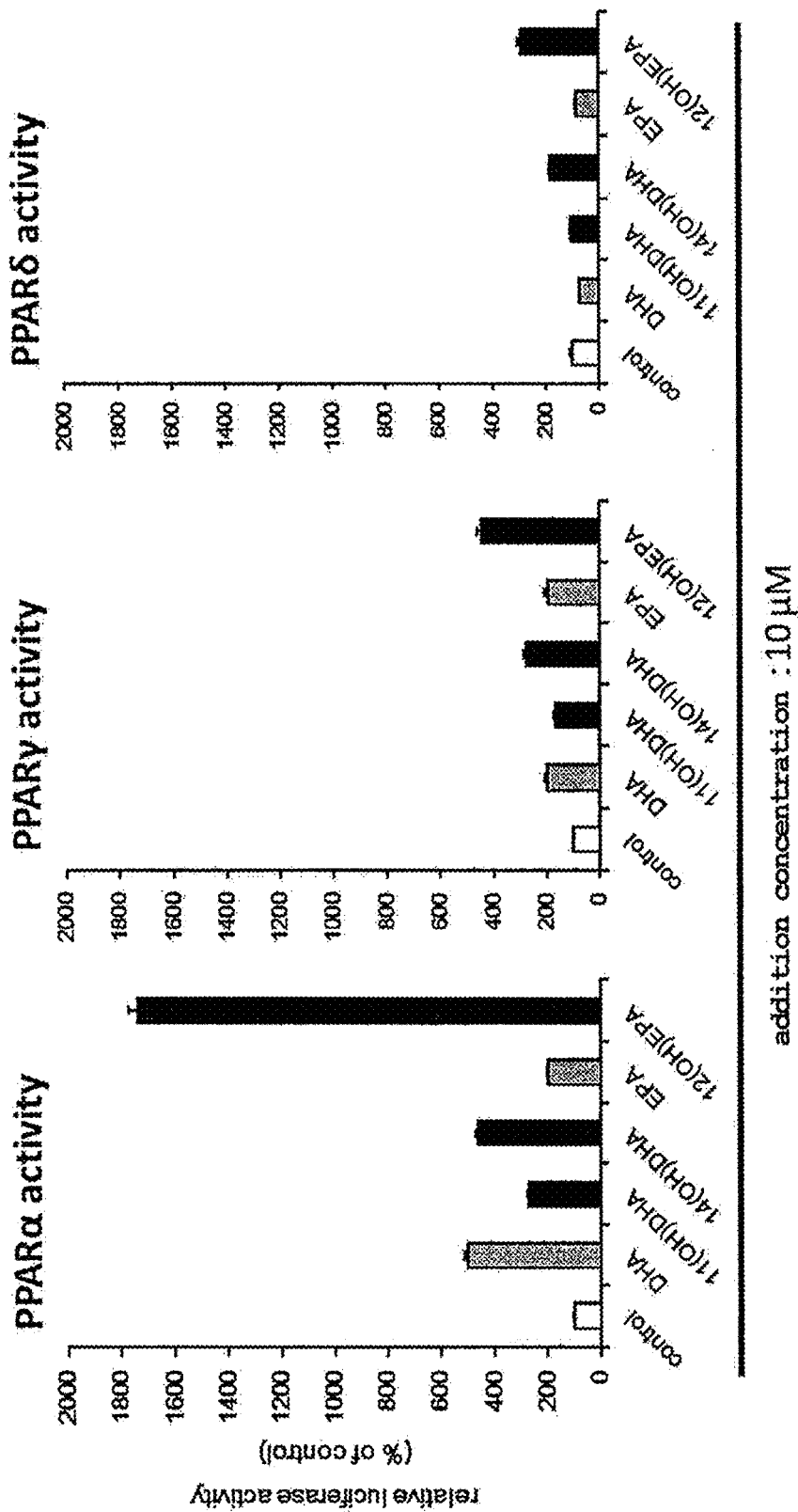

SEQUENCE LISTING

```
<160> NUMBER OF SEQ ID NOS: 2

<210> SEQ ID NO 1
<211> LENGTH: 1590
<212> TYPE: DNA
<213> ORGANISM: Clostridium
<220> FEATURE:
<221> NAME/KEY: CDS
<222> LOCATION: (1)..(1590)

<400> SEQUENCE: 1 atg gaa aat act att tta aaa act agg aag atc ttc tta gta gga gga      48
Met Glu Asn Thr Ile Leu Lys Thr Arg Lys Ile Phe Leu Val Gly Gly
1               5                   10                  15 gga att gct tcc cta gct agt gct gtt tac ttt att caa gag gga cat      96
Gly Ile Ala Ser Leu Ala Ser Ala Val Tyr Phe Ile Gln Glu Gly His
            20                  25                  30 att cct cct gat aac atc tat ata ttt gag caa tta gat tgt ctt ggt     144
Ile Pro Pro Asp Asn Ile Tyr Ile Phe Glu Gln Leu Asp Cys Leu Gly
        35                  40                  45
```

```
gga agc atg gat gga gct ggt gat aat att aat ggt ttc ata gct cat      192
Gly Ser Met Asp Gly Ala Gly Asp Asn Ile Asn Gly Phe Ile Ala His
     50              55                  60 ggt tct aga atg ttt gat aaa gaa gct tac gct tgt tgt tat gat cta      240
Gly Ser Arg Met Phe Asp Lys Glu Ala Tyr Ala Cys Cys Tyr Asp Leu
 65              70                  75                  80 ttc tca aga gtt cct cta tca aag aat tct aac atg aca att tta gat      288
Phe Ser Arg Val Pro Leu Ser Lys Asn Ser Asn Met Thr Ile Leu Asp
                 85                  90                  95 gat ttt aat aaa ttt aat aaa gat act aaa ttt aat aga tca gct gtt      336
Asp Phe Asn Lys Phe Asn Lys Asp Thr Lys Phe Asn Arg Ser Ala Val
            100                 105                 110 agg ctt att gga gaa aat gct gaa aag att gat gtt ctt tct ttt gaa      384
Arg Leu Ile Gly Glu Asn Ala Glu Lys Ile Asp Val Leu Ser Phe Glu
        115                 120                 125 ctt tca aaa gca gac caa ctt gca tta agc agt atg ata atc caa cct      432
Leu Ser Lys Ala Asp Gln Leu Ala Leu Ser Ser Met Ile Ile Gln Pro
    130                 135                 140 gaa ttc aaa ttt gat aaa ata aga ata tgc gat tgc ttt act cct gat      480
Glu Phe Lys Phe Asp Lys Ile Arg Ile Cys Asp Cys Phe Thr Pro Asp
145                 150                 155                 160 ttc ttt aaa aca aat ttc tgg tat atg tgg gca aca act ttt gca ttc      528
Phe Phe Lys Thr Asn Phe Trp Tyr Met Trp Ala Thr Thr Phe Ala Phe
                165                 170                 175 caa cct tgg cat agt gca gtt gaa ttc aaa aga tat ctt cac aga ttt      576
Gln Pro Trp His Ser Ala Val Glu Phe Lys Arg Tyr Leu His Arg Phe
            180                 185                 190 ata cat gaa ttt cct cat gtt aca gat atg gca gga gtt aga cat tca      624
Ile His Glu Phe Pro His Val Thr Asp Met Ala Gly Val Arg His Ser
        195                 200                 205 aga tat att caa tat gat tca ata att gaa cca ata att gaa tac tta      672
Arg Tyr Ile Gln Tyr Asp Ser Ile Ile Glu Pro Ile Ile Glu Tyr Leu
    210                 215                 220 aaa aac tct ggt gtc cac ttt att atg gaa gtt aaa gta aat gat tta      720
Lys Asn Ser Gly Val His Phe Ile Met Glu Val Lys Val Asn Asp Leu
225                 230                 235                 240 gaa ttt aaa gaa ttt aat gga aag aaa gct gtt aat aaa ata ctt tat      768
Glu Phe Lys Glu Phe Asn Gly Lys Lys Ala Val Asn Lys Ile Leu Tyr
                245                 250                 255 act aaa aaa gat aga aat gaa gaa ata aat gta aag cct gaa gat ctt      816
Thr Lys Lys Asp Arg Asn Glu Glu Ile Asn Val Lys Pro Glu Asp Leu
            260                 265                 270 gta tta gtt aca att ggt tct atg act gct tgc ttt gat gtt ggt gat      864
Val Leu Val Thr Ile Gly Ser Met Thr Ala Cys Phe Asp Val Gly Asp
        275                 280                 285 aat gaa acc cca act gtt ata aaa gat aag tat gca gat gga act tgg      912
Asn Glu Thr Pro Thr Val Ile Lys Asp Lys Tyr Ala Asp Gly Thr Trp
    290                 295                 300 tct ctt tgg gaa aac ata gct aaa aaa gac cct tta ttt ggt cat cca      960
Ser Leu Trp Glu Asn Ile Ala Lys Lys Asp Pro Leu Phe Gly His Pro
305                 310                 315                 320 gaa gta ttt aat act cgt gta aat gaa tca ctt tgg gaa tca ata act     1008
Glu Val Phe Asn Thr Arg Val Asn Glu Ser Leu Trp Glu Ser Ile Thr
                325                 330                 335 atg aca ttt aaa aca cca cta ttt ttt aat tta gta aat gaa ttc tgt     1056
Met Thr Phe Lys Thr Pro Leu Phe Phe Asn Leu Val Asn Glu Phe Cys
            340                 345                 350 agt ggt act gga acc gaa ttt aca ttt aaa gat tca aac tgg ttt tta     1104
Ser Gly Thr Gly Thr Glu Phe Thr Phe Lys Asp Ser Asn Trp Phe Leu
        355                 360                 365
```

-continued

```
tca ata gtt tta cct cat caa cca tac ttt aaa tct caa tct aaa gat    1152
Ser Ile Val Leu Pro His Gln Pro Tyr Phe Lys Ser Gln Ser Lys Asp
    370             375                 380 att caa gta gct tgg ggt tat gca tta cat cct gat aaa gaa ggt aat    1200
Ile Gln Val Ala Trp Gly Tyr Ala Leu His Pro Asp Lys Glu Gly Asn
385             390                 395                 400 ttt gtt cat aaa aaa atg tat gat tgc aat ggt aga gaa ata ctt gaa    1248
Phe Val His Lys Lys Met Tyr Asp Cys Asn Gly Arg Glu Ile Leu Glu
                405                 410                 415 gaa att ata ggc tta atg gga ttt gat aaa tat aaa gat gaa ata tta    1296
Glu Ile Ile Gly Leu Met Gly Phe Asp Lys Tyr Lys Asp Glu Ile Leu
            420                 425                 430 gaa tct gct ata tgc aga cct tgt gta atg cca ttt ata aca agc cag    1344
Glu Ser Ala Ile Cys Arg Pro Cys Val Met Pro Phe Ile Thr Ser Gln
        435                 440                 445 ttc tta act aga aca tat gga gat aga cct gat gtt att cca aaa tcc    1392
Phe Leu Thr Arg Thr Tyr Gly Asp Arg Pro Asp Val Ile Pro Lys Ser
    450                 455                 460 tct cac aat tta gca ttc tta ggt caa ttc tgt gaa ata cct gat gat    1440
Ser His Asn Leu Ala Phe Leu Gly Gln Phe Cys Glu Ile Pro Asp Asp
465                 470                 475                 480 aca gta ttt act gtt gat tat tca gta aga tct gcc caa atg gct gta    1488
Thr Val Phe Thr Val Asp Tyr Ser Val Arg Ser Ala Gln Met Ala Val
                485                 490                 495 tat ggc tta tta gga tta tac tat aag gaa gtc act cct ata ttt aag    1536
Tyr Gly Leu Leu Gly Leu Tyr Tyr Lys Glu Val Thr Pro Ile Phe Lys
            500                 505                 510 gga gaa aat gat gtg aga gtt ctt tta ggt gca tta gca aca atg att    1584
Gly Glu Asn Asp Val Arg Val Leu Leu Gly Ala Leu Ala Thr Met Ile
        515                 520                 525 aaa taa                                                             1590
Lys

<210> SEQ ID NO 2
<211> LENGTH: 529
<212> TYPE: PRT
<213> ORGANISM: Clostridium

<400> SEQUENCE: 2

Met Glu Asn Thr Ile Leu Lys Thr Arg Lys Ile Phe Leu Val Gly Gly
1               5                   10                  15

Gly Ile Ala Ser Leu Ala Ser Ala Val Tyr Phe Ile Gln Glu Gly His
            20                  25                  30

Ile Pro Pro Asp Asn Ile Tyr Ile Phe Glu Gln Leu Asp Cys Leu Gly
        35                  40                  45

Gly Ser Met Asp Gly Ala Gly Asp Asn Ile Asn Gly Phe Ile Ala His
    50                  55                  60

Gly Ser Arg Met Phe Asp Lys Glu Ala Tyr Ala Cys Cys Tyr Asp Leu
65                  70                  75                  80

Phe Ser Arg Val Pro Leu Ser Lys Asn Ser Asn Met Thr Ile Leu Asp
                85                  90                  95

Asp Phe Asn Lys Phe Asn Lys Asp Thr Lys Phe Asn Arg Ser Ala Val
            100                 105                 110

Arg Leu Ile Gly Glu Asn Ala Glu Lys Ile Asp Val Leu Ser Phe Glu
        115                 120                 125

Leu Ser Lys Ala Asp Gln Leu Ala Leu Ser Ser Met Ile Ile Gln Pro
    130                 135                 140
```

```
Glu Phe Lys Phe Asp Lys Ile Arg Ile Cys Asp Cys Phe Thr Pro Asp
145                 150                 155                 160

Phe Phe Lys Thr Asn Phe Trp Tyr Met Trp Ala Thr Thr Phe Ala Phe
            165                 170                 175

Gln Pro Trp His Ser Ala Val Glu Phe Lys Arg Tyr Leu His Arg Phe
            180                 185                 190

Ile His Glu Phe Pro His Val Thr Asp Met Ala Gly Val Arg His Ser
            195                 200                 205

Arg Tyr Ile Gln Tyr Asp Ser Ile Ile Glu Pro Ile Ile Glu Tyr Leu
            210                 215                 220

Lys Asn Ser Gly Val His Phe Ile Met Glu Val Lys Val Asn Asp Leu
225                 230                 235                 240

Glu Phe Lys Glu Phe Asn Gly Lys Lys Ala Val Asn Lys Ile Leu Tyr
            245                 250                 255

Thr Lys Lys Asp Arg Asn Glu Glu Ile Asn Val Lys Pro Glu Asp Leu
            260                 265                 270

Val Leu Val Thr Ile Gly Ser Met Thr Ala Cys Phe Asp Val Gly Asp
            275                 280                 285

Asn Glu Thr Pro Thr Val Ile Lys Asp Lys Tyr Ala Asp Gly Thr Trp
290                 295                 300

Ser Leu Trp Glu Asn Ile Ala Lys Lys Asp Pro Leu Phe Gly His Pro
305                 310                 315                 320

Glu Val Phe Asn Thr Arg Val Asn Glu Ser Leu Trp Glu Ser Ile Thr
            325                 330                 335

Met Thr Phe Lys Thr Pro Leu Phe Phe Asn Leu Val Asn Glu Phe Cys
            340                 345                 350

Ser Gly Thr Gly Thr Glu Phe Thr Phe Lys Asp Ser Asn Trp Phe Leu
            355                 360                 365

Ser Ile Val Leu Pro His Gln Pro Tyr Phe Lys Ser Gln Ser Lys Asp
            370                 375                 380

Ile Gln Val Ala Trp Gly Tyr Ala Leu His Pro Asp Lys Glu Gly Asn
385                 390                 395                 400

Phe Val His Lys Lys Met Tyr Asp Cys Asn Gly Arg Glu Ile Leu Glu
            405                 410                 415

Glu Ile Ile Gly Leu Met Gly Phe Asp Lys Tyr Lys Asp Glu Ile Leu
            420                 425                 430

Glu Ser Ala Ile Cys Arg Pro Cys Val Met Pro Phe Ile Thr Ser Gln
            435                 440                 445

Phe Leu Thr Arg Thr Tyr Gly Asp Arg Pro Asp Val Ile Pro Lys Ser
            450                 455                 460

Ser His Asn Leu Ala Phe Leu Gly Gln Phe Cys Glu Ile Pro Asp Asp
465                 470                 475                 480

Thr Val Phe Thr Val Asp Tyr Ser Val Arg Ser Ala Gln Met Ala Val
            485                 490                 495

Tyr Gly Leu Leu Gly Leu Tyr Tyr Lys Glu Val Thr Pro Ile Phe Lys
            500                 505                 510

Gly Glu Asn Asp Val Arg Val Leu Leu Gly Ala Leu Ala Thr Met Ile
            515                 520                 525

Lys
```

PRODUCTION METHOD FOR RARE FATTY ACID USING NOVEL ENZYME, AND NOVEL RARE FATTY ACID

INCORPORATION-BY-REFERENCE OF MATERIAL ELECTRONICALLY SUBMITTED

Incorporated by reference in its entirety herein is a computer-readable nucleotide/amino acid sequence listing submitted concurrently herewith and identified as follows: 12,849 bytes ASCII (Text) file named "757843 Sequence-Listing.txt," created Sep. 29, 2021.

TECHNICAL FIELD

The present invention relates to a production method of a fatty acid. More particularly, it relates to the production of a hydroxylated fatty acid using an unsaturated fatty acid as a starting material, and characterized by a hydration reaction by a novel enzyme. Also, it relates to a novel rare fatty acid obtained by the production method.

BACKGROUND ART

A conjugated fatty acid represented by a conjugated linoleic acid (CLA) has been reported to have various physiological activities such as a lipid metabolism improving effect, an anti-arteriosclerosis effect, a body fat decreasing effect, and the like (non-patent documents 1-3), and is a functional lipid expected to be applicable to various fields of medicament, functional food, and the like (patent documents 1, 2). While CLA is known to be contained in dairy products and meat products since it is produced by microorganisms present in the stomach of ruminant and to be present in a small amount in vegetable oil, the detailed mechanism of production thereof is not known.

The present inventors reported that enzymes (CLA-HY, CLA-DC, CLA-DH) present in the bacterium of *Lactobacillus plantarum* are essential for the reaction to convert linoleic acid to conjugated linoleic acids (patent document 1). They reported the mechanism of a series of specific reactions and the presence of an intermediate and the like in the reactions of these enzymes (patent document 4). These enzyme reactions are effective for the production of a rare fatty acid which is an unsaturated fatty acid having 18 carbon atoms such as linoleic acid and the like and having a hydroxyl group or a carbonyl group at the 10-position. The present inventors further reported the presence of an enzyme in the *Lactobacillus acidophilus* bacterium (patent document 5). This enzyme is effective for the production of a rare fatty acid which is an unsaturated fatty acid having 18 carbon atoms such as linoleic acid and the like and having a hydroxyl group or a carbonyl group at the 13-position and is also useful for the production of rare fatty acids which include unsaturated fatty acids having 20 carbon atoms and a hydroxyl group or a carbonyl group at the 12-position and the 15-position, unsaturated fatty acids having 16 carbon atoms and a hydroxyl group or a carbonyl group at the 10-position, unsaturated fatty acids having 22 carbon atoms and a hydroxyl group or a carbonyl group, and rare fatty acids which are unsaturated fatty acids having 16 carbon atoms such as palmitoleic acid and a hydroxyl group or a carbonyl group at the 10-position. While the hydrating enzyme of *Lactobacillus acidophilus* is also effective in hydroxylating the 14-position of a docosahexaenoic acid having 22 carbon atoms, it shows no effect of imparting a hydroxyl group to the 11 position of a docosahexaenoic acid or a docosapentaenoic acid, and the production method of these fatty acids was unknown. The enzyme of *Lactobacillus acidophilus* is not effective in hydroxylating the 12-position of eicosapentaenoic acid, and the technique of hydrating eicosapentaenoic acid to hydroxylate the 12-position is not known.

In addition, it has been reported in recent years that oxo fatty acids such as 9-oxo-octadecadienoic acid, 13-oxo-octadecadienoic acid, and the like contained in tomato have an activity to improve lifestyle-related diseases, such as lipid metabolism improvement and the like (patent document 3, non-patent documents 4, 5). Furthermore, the inventors have reported that hydroxylated fatty acid and oxo fatty acid having 18 carbon atoms and having a hydroxyl group or an oxo group at the 10-position and 13-position have an activity to improve lifestyle-related diseases such as metabolism improvement, lipid metabolism improvement, and the like, an activity to improve intestinal barrier function, and an anti-inflammatory effect (patent documents 6, 7, 8, 9), and interest in hydroxylated fatty acids and oxo fatty acids is increasing. With respect to hydroxylated fatty acids and oxo fatty acids, however, synthesis of functional hydroxylated fatty acids or functional oxo fatty acids from unsaturated fatty acids is difficult since it is necessary to distinguish a plurality of double bonds present in a molecule of an unsaturated fatty acid and introduce a hydroxyl group or a carbonyl group thereinto at specific positions.

DOCUMENT LIST

Patent Documents patent document 1: JP-A-2007-259712
patent document 2: JP-A-2007-252333
patent document 3: JP-A-2011-184411
patent document 4: WO 2013/168310
patent document 5: WO 2015/111699
patent document 6: WO 2014/069227
patent document 7: WO 2014/129384
patent document 8: WO 2015/111700
patent document 9: WO 2015/111701

Non-Patent Documents non-patent document 1: Ha Y L, (1987), Carcinogenesis, vol. 8, no. 12, p. 1881-1887
non-patent document 2: Clement Ip, (1991), Cancer Res., vol. 51, p. 6118-6124
non-patent document 3: Kisun N L, (1994), Atherosclerosis, vol. 108, p. 19-25
non-patent document 4: Kim Y-I, (2011), Mol. Nutr. Food Res., vol. 55, p. 585-593
non-patent document 5: Kim Y-I, (2012), PLoS ONE, vol. 7, no. 2, e31317

SUMMARY OF INVENTION

Technical Problem

It is an object of the present invention to provide a method for producing a hydroxylated fatty acid from an unsaturated fatty acid as a starting material and using a novel enzyme, without requiring oxygen.

Solution to Problem

The present inventors have clarified the reaction in which soil-derived *Clostridium* microorganisms hydroxylate the 11-position of docosahexaenoic acid, which is an unsaturated fatty acid having 22 carbon atoms, and have identified a novel enzyme (FA-HYcx1) involved in the production.

The present inventors have found a method for converting an unsaturated fatty acid having 20 carbon atoms into a hydroxylated fatty acid by using a novel enzyme (FA-HYcx1) and further a method for oxidizing the hydroxyl group of the produced substance by a chemical reaction.

The present inventors have produced hydroxylated fatty acids and oxo fatty acids having previously unknown structures by a new production method of rare fatty acids by using a novel enzyme (FA-HYcx1) and have found that these fatty acids have an activity as agonists of nuclear receptors PPARα, PPARγ, and PPARδ.

To be specific, the present inventors have found that 11-hydroxy-cis-4,cis-7,cis-13,cis-16,cis-19-docosapentaenoic acid is produced from docosahexaenoic acid (DHA) by using a novel enzyme (FA-HYcx1) and further that 11-oxo-cis-4,cis-7,cis-13,cis-16,cis-19-docosapentaenoic acid is produced from 11-hydroxy-cis-4,cis-7,cis-13,cis-16,cis-19-docosapentaenoic acid by introducing a chemical oxidation method using chromic acid.

The present inventors have further studied and found that 11-hydroxy-cis-7,cis-13,cis-16,cis-19-docosatetraenoic acid is produced from docosapentaenoic acid (DPA) by using a novel enzyme (FA-HYcx1) and that a fatty acid with hydroxylated 11-position is produced using an unsaturated fatty acid having 22 carbon atoms and a cis double bond at the 10-position as a substrate.

In addition, the present inventors have found that fatty acids with the hydroxylated 10-position and the hydroxylated 12-position are produced using a novel enzyme (FA-HYcx1) and an unsaturated fatty acid having 18 carbon atoms and a cis-type double bond at the 9-position (linoleic acid, γ-linolenic acid, α-linolenic acid, oleic acid, etc.) and unsaturated fatty acid having 20 carbon atoms and a cis-type double bond at the 11-position (eicosapentaenoic acid, dihomo-γ-linolenic acid, mead acid, arachidonic acid, etc.) as a substrate, respectively. They have found that the hydration enzyme (FA-HY) in patent document 5 does not hydrate the cis double bond at the 11-position of eicosapentaenoic acid, but the novel enzyme (FA-HYcx1) hydrates the cis double bond at the 11-position, and 12-hydroxy-cis-5,cis-8,cis-14,cis-17-eicosatetraenoic acid which is a fatty acid with the hydroxylated 12-position is produced.

The present inventors have found that the hydroxylated fatty acids which are resultant products obtained by the present invention include a fatty acid having a previously unknown structure, i.e., a novel substance. In addition, the present inventors have found that the hydroxylated fatty acids including a novel fatty acid have an activity as an agonist of nuclear receptors PPARα, PPARγ, and PPARγ. Therefore, the aforementioned hydroxylated fatty acid can be utilized as metabolism improving agents and the like.

Also, the present inventors have found that an oxo fatty acid is produced using such hydroxylated fatty acid as a starting material and introducing a chemical oxidation method using chromic acid. The resultant product, an oxo fatty acid, is also a novel substance having a previously unknown structure. The oxo fatty acids including a novel fatty acid are also considered to have an activity as an agonist of nuclear receptors PPARγ, PPARγ, and PPARγ. Thus, the aforementioned oxo fatty acid can also be utilized as a metabolism improving agent and the like. The present invention was completed based on the above findings.

Accordingly, the present invention provides the following:

[1] An enzyme protein of any of the following (a) (c):
  (a) an enzyme protein consisting of the amino acid sequence shown in SEQ ID NO: 2,
  (b) a protein comprising an amino acid sequence resulting from deletion and/or substitution and/or insertion and/or addition of one or plural amino acids in the amino acid sequence shown in SEQ ID NO: 2, and having an enzyme activity to catalyze a hydration reaction,
  (c) a protein encoded by a base sequence that hybridizes to a nucleic acid consisting of a complementary chain sequence of the base sequence shown in SEQ ID NO: 1 under stringent conditions, and having an enzyme activity to catalyze a hydration reaction;
[2] a bacterium of the genus *Clostridium* or a bacterial homogenate thereof, comprising the enzyme protein of [1];
[3] a nucleic acid encoding the enzyme protein of [1];
[4] a vector comprising the nucleic acid of [3];
[5] a host cell transformed with the vector of [4];
[6] a method for producing an enzyme, comprising culturing the host cell of [5], and recovering the enzyme protein of [1] from the culture;
[7] a method for producing a hydroxylated fatty acid having 22 carbon atoms and a hydroxyl group at the 11-position from an unsaturated fatty acid having 22 carbon atoms and a cis-type double bond at the 10-position by a hydration reaction using the enzyme protein of [1];
[8] a method for producing an oxo fatty acid having 22 carbon atoms and a carbonyl group at the 11-position, comprising inducing a hydroxylated fatty acid having 22 carbon atoms and a hydroxyl group at the 11-position from an unsaturated fatty acid having 22 carbon atoms and a cis-type double bond at the 10-position by a hydration reaction using the enzyme protein of [1], and subjecting the hydroxylated fatty acid to a dehydrogenation reaction or chemical oxidation;
[9] a method for producing a hydroxylated fatty acid having 20 carbon atoms and a hydroxyl group at the 12-position from an unsaturated fatty acid having 20 carbon atoms and a cis-type double bond at the 11-position by a hydration reaction using the enzyme protein of [1];
[10] a method for producing an oxo fatty acid having 20 carbon atoms and a carbonyl group at the 12-position, comprising inducing a hydroxylated fatty acid having 20 carbon atoms and a hydroxyl group at the 12-position from an unsaturated fatty acid having 20 carbon atoms and a cis-type double bond at the 11-position by a hydration reaction using the enzyme protein of [1], and subjecting the hydroxylated fatty acid to a dehydrogenation reaction or chemical oxidation;
[11] a method for producing a hydroxylated fatty acid having 18 carbon atoms and a hydroxyl group at the 10-position from an unsaturated fatty acid having 18 carbon atoms and a cis-type double bond at the 9-position by a hydration reaction using the enzyme protein of [1];
[12] a method for producing an oxo fatty acid having 18 carbon atoms and a carbonyl group at the 10-position, comprising inducing a hydroxylated fatty acid having 18 carbon atoms and a hydroxyl group at the 10-position from an unsaturated fatty acid having 18 carbon atoms and a cis-type double bond at the 9-position by a hydration reaction using the enzyme protein of [1], and subjecting the hydroxylated fatty acid to a dehydrogenation reaction or chemical oxidation;

[13] the method of [7] or [8], wherein the unsaturated fatty acid having 22 carbon atoms and a cis-type double bond at the 10-position is docosahexaenoic acid or docosapentaenoic acid;

[14] the method of [9] or [10], wherein the unsaturated fatty acid having 20 carbon atoms and a cis-type double bond at the 11-position is eicosapentaenoic acid, dihomo-γ-linolenic acid, mead acid, eicosatetraenoic acid, eicosatrienoic acid, or arachidonic acid;

[15] the method of [11] or [12], wherein the unsaturated fatty acid having 18 carbon atoms and a cis-type double bond at the 9-position is linoleic acid, α-linolenic acid, γ-linolenic acid, or oleic acid;

[16] 11-hydroxy-cis-4,cis-7,cis-13,cis-16,cis-19-docosapentaenoic acid or 11-hydroxy-cis-7,cis-13,cis-16,cis-19-docosatetraenoic acid produced by the method of [7];

[17] 12-hydroxy-cis-5,cis-8,cis-14,cis-17-eicosatetraenoic acid produced by the method of [9];

[18] 11-oxo-cis-4,cis-7,cis-13,cis-16,cis-19-docosapentaenoic acid or 11-oxo-cis-7,cis-13,cis-16,cis-19-docosatetraenoic acid produced by the method of [8];

[19] 12-oxo-cis-5,cis-8,cis-14,cis-17-eicosatetraenoic acid produced by the method of [10];

[20] a fatty acid-containing material comprising the hydroxylated fatty acid or oxo fatty acid of any one of [16] to [19];

[21] the fatty acid-containing material of [20], wherein the material is a pharmaceutical composition;

[22] the fatty acid-containing material of [20], wherein the material is a food or a food additive;

[23] the fatty acid-containing material of [20], wherein the material is a cosmetic or a cosmetic additive;

[24] the fatty acid-containing material of [20], wherein the feed is a feed additive;

[25] use of a bacterium of the genus *Clostridium* or a bacterial homogenate thereof comprising the enzyme protein of [1], in the production of the hydroxylated fatty acid or the oxo fatty acid of any one of [16] to [19].

Advantageous Effects of Invention

The present inventors have found a fatty acid hydration enzyme (FA-HYcx1) not known conventionally, a method for converting unsaturated fatty acids having 22, 20, and 18 carbon atoms to hydroxylated fatty acids, and further a method for oxidizing a hydroxyl group of the resulting substance by chemical reactions. The rare fatty acid and the like produced by such method are extremely useful since they can be used in various fields of pharmaceutical composition, food, cosmetic, and the like. A novel rare fatty acid can be produced by the production using the novel enzyme, and since the novel rare fatty acid also has an activity as an agonist of nuclear receptors PPARα, PPARγ, and PPARδ, the novel rare fatty acid becomes a useful substance in various fields such as pharmaceutical composition, food, cosmetic, and the like.

BRIEF DESCRIPTION OF DRAWINGS

FIG. 1 shows the results of the PPARα, PPARγ, and PPARδ agonist activities of DHA-derived and EPA-derived rare fatty acids. The vertical axis shows relative luciferase activity.

DESCRIPTION OF EMBODIMENTS

The present invention is explained in detail below.
The present invention provides a novel fatty acid hydration enzyme "FA-HYcx1".
Specifically, the novel enzyme "FA-HYcx1" of the present invention is
(a) an enzyme protein consisting of the amino acid sequence shown in SEQ ID NO: 2,
(b) a protein comprising an amino acid sequence resulting from deletion and/or substitution and/or insertion and/or addition of one or plural amino acids in the amino acid sequence shown in SEQ ID NO: 2, and having an enzyme activity possessed by an enzyme protein consisting of the amino acid sequence shown in SEQ ID NO: 2, or
(c) a protein encoded by a base sequence that hybridizes to a nucleic acid consisting of a complementary chain sequence of the base sequence shown in SEQ ID NO: 1 under stringent conditions, and having an enzyme activity possessed by an enzyme protein consisting of the amino acid sequence shown in SEQ ID NO: 2.

More specific examples of the above-mentioned (b) include a protein containing (i) an amino acid sequence resulting from deletion of 1-20, preferably 1-10, more preferably 1—several (5, 4, 3, or 2) amino acids in the amino acid sequence shown in SEQ ID NO: 2, (ii) an amino acid sequence resulting from addition of 1-20, preferably 1-10, more preferably 1—several number (5, 4, 3, or 2) amino acids in the amino acid sequence shown in SEQ ID NO: 2, (iii) an amino acid sequence resulting from insertion of 1-20, preferably 1-10, more preferably 1—several (5, 4, 3, or 2) amino acids in the amino acid sequence shown in SEQ ID NO: 2, (iv) an amino acid sequence resulting from substitution of 1-20, preferably 1-10, more preferably 1—several (5, 4, 3, or 2) amino acids by other amino acids in the amino acid sequence shown in SEQ ID NO: 2, or (v) an amino acid sequence obtained by combining them. When amino acids with similar properties (e.g., glycine and alanine, valine and leucine and isoleucine, serine and threonine, aspartic acid and glutamic acid, asparagine and glutamine, lysin and arginine, cysteine and methionine, phenylalanine and tyrosine, etc.) are substituted with each other and the like, a greater number of substitutions and the like are possible.

When amino acids are deleted, substituted, or inserted as mentioned above, the positions of deletion, substitution, and insertion are not particularly limited as long as the above-mentioned enzyme activity is maintained.

In the above-mentioned (c), the "stringent conditions" are conditions under which nucleotide sequences having high identity, for example, identity of 70, 80, 90, 95 or 99% or above, hybridize to each other and nucleotide sequences having identity lower than that do not hybridize; specifically, conditions of washing once, more preferably 2-3 times, at the salt concentration and temperature corresponding to those in the washing conditions of general Southern hybridization (60° C., 1×SSC, 0.1% SDS, preferably, 0.1×SSC, 0.1% SDS, more preferably, 68° C., 0.1×SSC, 0.1% SDS) and the like. Particularly, conditions severer than the conditions of washing 3 times at 68° C., 0.1×SSC, 0.1% SDS are to be also referred to as highly stringent conditions.

reaction 1

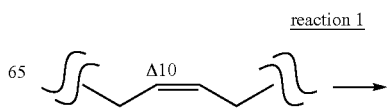

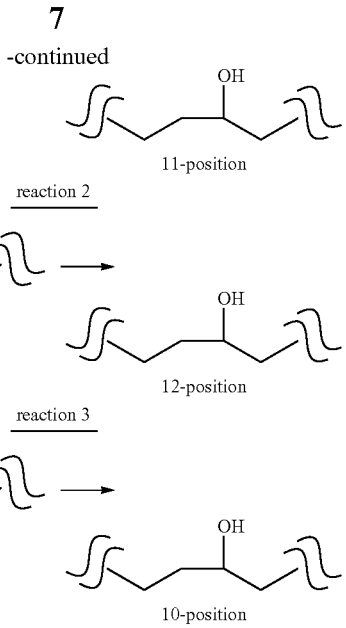

With regard to the above-mentioned (b) and (c), the enzyme activity that an enzyme protein consisting of the amino acid sequence shown in SEQ ID NO: 2 has is not particularly limited as long as it shows at least one, preferably all, of (1) an enzyme activity that is capable of converting an unsaturated fatty acid having 22 carbon atoms and a cis-type double bond at the 10-position (hereinafter sometimes to be abbreviated as a "cis-10 unsaturated fatty acid") as a substrate to a hydroxylated fatty acid having 22 carbon atoms and a hydroxyl group at the 11-position (hereinafter sometimes to be abbreviated as an "11-hydroxy fatty acid") (reaction 1), (2) an enzyme activity that is capable of converting an unsaturated fatty acid having 20 carbon atoms and a cis-type double bond at the 11-position (hereinafter sometimes to be abbreviated as a "cis-11 unsaturated fatty acid") as a substrate to a hydroxylated fatty acid having 20 carbon atoms and a hydroxyl group at the 12-position (hereinafter sometimes to be abbreviated as a "12-hydroxy fatty acid") (reaction 2), and (3) an enzyme activity that is capable of converting an unsaturated fatty acid having 18 carbon atoms and a cis-type double bond at the 9-position (hereinafter sometimes to be abbreviated as a "cis-9 unsaturated fatty acid") as a substrate to a hydroxylated fatty acid having 18 carbon atoms and a hydroxyl group at the 10-position (hereinafter sometimes to be abbreviated as a "10-hydroxy fatty acid") (reaction 3).

The above-mentioned "cis-10 unsaturated fatty acid", "cis-11 unsaturated fatty acid", and "cis-9 unsaturated fatty acid" are not particularly limited as long as they are an unsaturated fatty acid having 22 carbon atoms and a cis-type double bond at the 10-position, an unsaturated fatty acid having 20 carbon atoms and a cis-type double bond at the 11-position, and an unsaturated fatty acid having 18 carbon atoms and a cis-type double bond at the 9-position, respectively, and, for example, monovalent unsaturated fatty acids, divalent unsaturated fatty acids, trivalent unsaturated fatty acids, tetravalent unsaturated fatty acids, pentavalent unsaturated fatty acids, and the like can be mentioned. In the present specification, the "fatty acid" encompasses not only a free acid but also ester, a salt with basic compound, and the like.

The FA-HYcx1 of the present invention can be produced as a recombinant protein of SEQ ID NO: 2, by synthesizing the gene of SEQ ID NO: 1 encoding FA-HYcx1, subcloning same into a suitable vector, introducing same into a suitable host such as *Escherichia coli* and the like, and culturing same. FA-HYcx1 may be a purified one or a crudely purified one. Alternatively, the enzyme may be expressed in a bacterium such as *Escherichia coli* and the like and the bacterium itself may be used or a culture medium thereof may be used. Furthermore, the enzyme may be of a free type, or may be immobilized by various carriers.

The gene of SEQ ID NO: 1 can be obtained in the form of a DNA that encodes the full length by chemical synthesis of a DNA strand or connection of a synthesized partially overlapping oligo DNA short strand to each other with a PCR method (overlap PCR method) or a Gibson Assembly method. The advantage of constructing a full-length DNA by combining chemical synthesis, PCR, or Gibson Assembly method is that the codons to be used can be designed over the full length of the CDS according to the host into which the DNA is introduced. In expressing a heterologous DNA, the protein expression level is expected to be increased by converting the DNA sequence into codons that are frequently used in the host organism. For the data on codon usage frequency in the host to be used, for example, the genetic code usage frequency database (http://www.kazusa.or.jp/codon/index.html) published on the website of the Kazusa DNA Research Institute can be used, or the literature describing the frequency of codon usage in each host may be referred to. By referring to the obtained data and the DNA sequence to be introduced, the codons used in the DNA sequence and not frequently used in the host may be converted to codons that are frequently used and encode the same amino acid. For example, when the host cell is *Escherichia coli*, a gene encoding FA-HYcx1 optimized for codon use in *E. coli* and microorganisms in general can be used.

As a vector containing a nucleic acid encoding FA-HYcx1 of the present invention, one which is suitable for a host cell into which the vector is to be introduced may be appropriately selected according to the object (e.g., protein expression) and can be used. In the case of an expression vector, it contains the nucleic acid of the present invention, which is operably linked to an appropriate promoter, and preferably contains a transcription termination signal, i.e., a terminator region, at the downstream of the nucleic acid of the present invention. Furthermore, for selection of a transformant, it can also contain selection marker genes (drug resistance gene, gene that complements auxotrophic mutation, etc.). Also, it may contain a sequence encoding a tag sequence that is useful for separation and purification of the expressed protein and the like. In addition, the vector may be incorporated into the genome of a target host cell. The vector of the present invention can be introduced into a target host cell by a transformation method known per se such as a competent cell method, a protoplast method, a calcium phosphate coprecipitation method, and the like.

In the present invention, the "host cell" may be any cell as long as it can express a vector containing a nucleic acid encoding FA-HYcx1 of the present invention, and bacteria, yeast, fungi, higher eukaryotic cells, and the like can be mentioned. Examples of the bacteria include gram-positive bacteria such as *Bacillus, Streptomyces*, and the like and gram-negative bacteria such as *Escherichia coli* and the like. A recombinant cell into which a vector containing a nucleic acid encoding FA-HYcx1 was introduced can be cultured by a method known per se which is suitable for the host cell.

In the present invention, "purification" of FA-HYcx1 can be performed by a method known per se, for example, cells collected by centrifugation and the like are homogenated by ultrasonication or glass beads and the like, and solid such as cell debris is removed by centrifugation and the like to give a crude enzyme solution, which is further subjected to a salting out method using ammonium sulfate, sodium sulfate, and the like, chromatography such as ion exchange chromatography, gel filtration chromatography, affinity chromatography, and the like, gel electrophoresis, and the like.

The FA-HYcx1 of the present invention has an enzyme activity that is capable of converting a cis-10 unsaturated fatty acid, a cis-11 unsaturated fatty acid, and a cis-9 unsaturated fatty acid as a substrate to an 11-hydroxy fatty acid, a 12-hydroxy fatty acid, and a 10-hydroxy fatty acid, respectively, as described above. Therefore, the present invention also provides [1] a method for producing an 11-hydroxy fatty acid from a cis-10 unsaturated fatty acid by a hydration reaction using the FA-HYcx1 of the present invention (production method 1), [2] a method for producing a 12-hydroxy fatty acid from a cis-11 unsaturated fatty acid by a hydration reaction using the FA-HYcx1 of the present invention (production method 2), [3] a method for producing a 10-hydroxy fatty acid from a cis-9 unsaturated fatty acid by a hydration reaction using the FA-HYcx1 of the present invention (production method 3).

Examples of the "cis-10 unsaturated fatty acid" in the production method 1 of the present invention include docosahexaenoic acid, docosapentaenoic acid, and the like.

Examples of the "11-hydroxy fatty acid" produced by the production method 1 of the present invention include 11-hydroxy-cis-4,cis-7,cis-13,cis-16,cis-19-docosapentaenoic acid induced from docosahexaenoic acid, 11-hydroxy-cis-7,cis-13,cis-16,cis-19-docosatetraenoic acid induced from docosapentaenoic acid, and the like.

Examples of the "cis-11 unsaturated fatty acid" in the production method 2 of the present invention include eicosapentaenoic acid, dihomo-γ-linolenic acid, mead acid, eicosatetraenoic acid, eicosatrienoic acid, arachidonic acid, and the like.

Examples of the "12-hydroxy fatty acid" produced by the production method 2 of the present invention include 12-hydroxy-cis-5,cis-8,cis-14,cis-17-eicosatetraenoic acid induced from eicosapentaenoic acid, 12-hydroxy-cis-8,cis-14-eicosadienoic acid induced from dihomo-γ-linolenic acid, 12-hydroxy-cis-5,cis-8-eicosadienoic acid induced from mead acid, 12-hydroxy-cis-8,cis-14,cis-17-eicosatrienoic acid induced from eicosatetraenoic acid, 12-hydroxy-cis-14,cis-17-eicosadienoic acid induced from eicosatrienoic acid, 12-hydroxy-cis-5,cis-8,cis-14-eicosatrienoic acid induced from arachidonic acid, and the like.

Examples of the "cis-9 unsaturated fatty acid" in the production method 3 of the present invention include linoleic acid, α-linolenic acid, γ-linolenic acid, oleic acid, and the like.

Examples of the "10-hydroxy fatty acid" produced by the production method 3 of the present invention include 10-hydroxy-cis-12-octadecenoic acid induced from linoleic acid, 10-hydroxy-cis-12,cis-15-octadecadienoic acid induced from α-linolenic acid, 10-hydroxy-cis-6,cis-12-octadecadienoic acid induced from γ-linolenic acid, 10-hydroxyoctadecanoic acid induced from oleic acid, and the like.

The hydration reaction may be performed, for example, a cis-10 unsaturated fatty acid, a cis-11 unsaturated fatty acid, or a cis-9 unsaturated fatty acid is brought into contact with FA-HYcx1 of the present invention. Specifically, it may be performed by mixing an unsaturated fatty acid, which is a substrate, and FA-HYcx1 of the present invention at suitable concentrations and incubating the mixture in a suitable buffer (e.g., phosphate buffer, tris buffer, borate buffer, etc.). The substrate concentration is, for example, 1-1000 g/L, preferably 10-500 g/L, more preferably 20-250 g/L. The amount of the aforementioned FA-HY to be added is, for example, 0.001-10 mg/ml, preferably 0.1-5 mg/ml, more preferably 0.2-2 mg/ml.

A "cofactor" may be used for the hydration reactions (reactions 1-3) and, for example, FAD and the like can be used. The addition concentration may be any as long as the hydration reaction proceeds efficiently. It is preferably 0.001-20 mM, more preferably 0.01-10 mM.

Furthermore, an "activator" may be used for the hydration reactions and, for example, one or two compounds selected from the group consisting of NADH and NADPH can be mentioned. The addition concentration may be any as long as the hydration reaction proceeds efficiently. It is preferably 0.1-20 mM, more preferably 1-10 mM.

The hydration reactions are desirably performed within the ranges of preferable temperature and preferable pH of FA-HYcx1 of the present invention. For example, the reaction temperature is 5-50° C., preferably 20-45° C. The pH of the reaction mixture is, for example, pH 4-10, preferably pH 5-9. The reaction time is not particularly limited and itis, for example, 10 min-72 hr, preferably 30 min-36 hr.

In one preferable embodiment of the present invention, FA-HYcx1 of the present invention is provided to the reaction system in the form of recombinant cells (e.g., *Escherichia coli*, *Bacillus subtilis*, yeast, insect cells, animal cells, etc.) into which an expression vector containing a nucleic acid encoding same was introduced. In this case, the hydration reactions can also be performed by culturing the cells in a liquid medium which is suitable for the culture of the cells and to which a substrate and, where necessary, a cofactor and an activator were added.

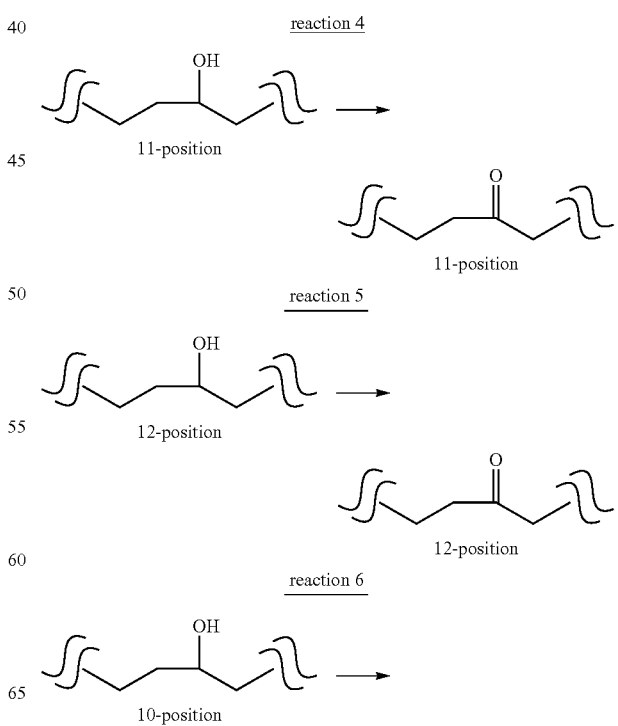

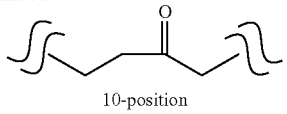

10-position

Furthermore, by chemical oxidation using chromic acid, an oxo fatty acid having 22 carbon atoms and a carbonyl group at the 11-position (hereinafter sometimes to be abbreviated as an "11-oxo fatty acid") is produced from an 11-hydroxy fatty acid obtained by the production methods 1-3 of the present invention (reaction 4), an oxo fatty acid having 20 carbon atoms and a carbonyl group at the 12-position (hereinafter sometimes to be abbreviated as a "12-oxo fatty acid") is produced from a 12-hydroxy fatty acid obtained by the production methods 1-3 of the present invention (reaction 5), and an oxo fatty acid having 18 carbon atoms and a carbonyl group at the 10-position (hereinafter sometimes to be abbreviated as a "10-oxo fatty acid") is produced from a 10-hydroxy fatty acid obtained by the production methods 1-3 of the present invention (reaction 6).

Therefore, the present invention also provides [4] a method for producing an 11-oxo fatty acid by inducing an 11-hydroxy fatty acid from a cis-10 unsaturated fatty acid in a hydration reaction using the FA-HYcx1 of the present invention and subjecting the 11-hydroxy fatty acid to a chemical oxidation (production method 4), [5] a method for producing a 12-oxo fatty acid by inducing a 12-hydroxy fatty acid from a cis-11 unsaturated fatty acid in a hydration reaction using the FA-HYcx1 of the present invention and subjecting the 12-hydroxy fatty acid to a chemical oxidation (production method 5), [6] a method for producing a 10-oxo fatty acid by inducing a 10-hydroxy fatty acid from a cis-9 unsaturated fatty acid in a hydration reaction using the FA-HYcx1 of the present invention and subjecting the 10-hydroxy fatty acid to a chemical oxidation (production method 6).

The "cis-10 unsaturated fatty acid", the "cis-11 unsaturated fatty acid", and the "cis-9 unsaturated fatty acid" in the production methods 4-6 of the present invention are the same as the substrates in the above-mentioned production methods 1-3.

Examples of the "11-oxo fatty acid" produced by the production method 4 of the present invention include 11-oxo-cis-4,cis-7,cis-13,cis-16,cis-19-docosapentaenoic acid induced from docosahexaenoic acid, 11-oxo-cis-7,cis-13,cis-16,cis-19-docosatetraenoic acid induced from docosapentaenoic acid, and the like.

Examples of the "12-oxo fatty acid" produced by the production method 5 of the present invention include 12-oxo-cis-5,cis-8,cis-14,cis-17-eicosatetraenoic acid induced from eicosapentaenoic acid, 12-oxo-cis-8,cis-14-eicosadienoic acid induced from dihomo-γ-linolenic acid, 12-oxo-cis-5,cis-8-eicosadienoic acid induced from mead acid, 12-oxo-cis-8,cis-14,cis-17-eicosatrienoic acid induced from eicosatetraenoic acid, 12-oxo-cis-14,cis-17-eicosadienoic acid induced from eicosatrienoic acid, 12-oxo-cis-5,cis-8,cis-14-eicosatrienoic acid induced from arachidonic acid, and the like.

Examples of the "10-oxo fatty acid" produced by the production method 6 of the present invention include 10-oxo-cis-12-octadecenoic acid induced from linoleic acid, 10-oxo-cis-12,cis-15-octadecadienoic acid induced from α-linolenic acid, 10-oxo-cis-6,cis-12-octadecadienoic acid induced from γ-linolenic acid, 10-oxooctadecanoic acid induced from oleic acid, and the like.

In the production methods 4-6 of the present invention, oxo fatty acids can be chemically obtained by chemical oxidation using chromic acid. For example, they can be performed by contacting an 11-hydroxy fatty acid, a 12-hydroxy fatty acid, or a 10-hydroxy fatty acid with an oxidizing agent (e.g., chromic acid etc. mentioned below).

Specifically, as the chemical oxidation, methods known per se, for example, chromic acid oxidation, preferably Jones oxidation and the like can be mentioned. As the chromic acid, salts and complexes of the compound such as anhydrous chromic acid $CrO_3$, chromic acid $H_2CrO_4$, and dichromic acid $H_2Cr_2O_7$ can be used.

Specifically, to anhydrous chromic acid (2.67 g) are added sulfuric acid (2.3 ml) and water (7.7 ml), and acetone (90 ml) is added thereto to give a chromic acid solution. 2 g of a hydroxylated fatty acid and 40 ml of acetone are added into an Erlenmeyer flask, and the above-mentioned chromic acid solution is added drop by drop on ice while stirring the mixture with a stirrer. When the solution turns from blue to the color of powdered green tea, the dropwise addition of the chromic acid solution is stopped and the reaction is quenched with isopropyl alcohol. The precipitated sediment is filtered with filter paper and placed in a separating funnel. Diethyl ether (150 ml) and Milli Q water (300 ml) are further added and the mixture is shaken well. The diethyl ether layer is washed several times with Milli Q water. After washing, to the diethyl ether layer is added an appropriate amount of sodium sulfate (anhydrous), the mixture is stirred, and the residual water is removed. The anhydrous sodium sulfate added is filtered out with filter paper, the obtained diethyl ether layer is concentrated in rotary evaporator, and the reaction product (an oxo fatty acid) and an unreacted substrate are extracted.

Extract obtained by an oxidation reaction with anhydrous chromic acid (mixture containing substrate and resultant product (an oxo fatty acid)) is subjected to moderate-pressure chromatography, and the solution eluted from the column is fractionated and is collected. The collected each fraction is analyzed by LC/MS and gas chromatography. The fractions containing only an oxo fatty acid are collected and are concentrated by rotary evaporator. A part of the obtained final resultant product is methylesterified, and the purity of an oxo fatty acid is evaluated by gas chromatography, whereby an oxo fatty acid with a purity of not less than 98% can be obtained.

An enzyme reaction by the dehydrogenase may be utilized for the oxidation reaction in the production methods 4-6 of the present invention, and the dehydrogenase is not particularly limited as long as it is an enzyme which is capable of utilizing an 11-hydroxy fatty acid, a 12-hydroxy fatty acid, or a 10-hydroxy fatty acid as a substrate and converting to an 11-oxo fatty acid, a 12-oxo fatty acid, and a 10-oxo fatty acid, respectively. For example, a hydroxylated fatty acid dehydrogenase derived from *Lactobacillus* is preferable. A dehydrogenase may be a purified one or a crudely purified one. Alternatively, a dehydrogenase may be expressed in a bacterium such as *Escherichia coli* and the like and the bacterium itself or culture medium thereof may be used. Furthermore, the enzyme may be of a free type, or immobilized by various carriers.

The dehydrogenation reaction may be performed, for example, by contacting an 11-hydroxy fatty acid, a 12-hydroxy fatty acid, or a 10-hydroxy fatty acid with the aforementioned dehydrogenase. Specifically, it may be performed by mixing an 11-hydroxy fatty acid, a 12-hydroxy fatty acid, or a 10-hydroxy fatty acid, which is a substrate, and a dehydrogenase at suitable concentrations and incubating the mixture in a suitable buffer (e.g., phosphate buffer, tris buffer, borate buffer, etc.). The substrate concentration is, for example, 0.01-100 g/L, preferably 0.05-50 g/L, more preferably 0.1-5 g/L. The amount of the dehydrogenase to be added is, for example, 0.001-10 mg/mL, preferably 0.005-1 mg/mL, more preferably 0.05-0.2 mg/mL.

A "cofactor" may be used for the dehydrogenation reaction and, for example, NAD, NADP, and the like can be used. The addition concentration may be any as long as the oxidation reaction proceeds efficiently. It is preferably 0.001-20 mM, more preferably 0.01-10 mM.

The dehydrogenation reaction is desirably performed within the ranges of preferable temperature and preferable pH of a dehydrogenase. For example, the reaction temperature is 5-50° C., preferably 20-45° C. The pH of the reaction mixture is, for example, pH 4-10, preferably pH 5-9. The reaction time is not particularly limited and it is, for example, 10 min-72 hr, preferably 30 min-36 hr.

In one embodiment of the present invention, a dehydrogenase is provided to the reaction system in the form of recombinant cells (e.g., *Escherichia coli*, *Bacillus subtilis*, yeast, insect cells, animal cells, etc.) into which an expression vector containing a nucleic acid encoding same is introduced. In this case, the oxidation reactions can also be performed by culturing the cells in a liquid medium which is suitable for the culture of the cells and to which a substrate and, where necessary, a cofactor and an activator were added.

The following hydroxylated fatty acids obtained by the production methods 1-6 of the present invention are novel fatty acids having unknown structures heretofore.

<Hydroxylated Fatty Acids>
11-Hydroxy-cis-4,cis-7,cis-13,cis-16,cis-19-docosapentaenoic acid
11-Hydroxy-cis-7,cis-13,cis-16,cis-19-docosatetraenoic acid
12-Hydroxy-cis-5,cis-8,cis-14,cis-17-eicosatetraenoic acid <Oxo Fatty Acids>
11-Oxo-cis-4,cis-7,cis-13,cis-16,cis-19-docosapentaenoic acid
11-Oxo-cis-7,cis-13,cis-16,cis-19-docosatetraenoic acid
12-Oxo-cis-5,cis-8,cis-14,cis-17-eicosatetraenoic acid The novel hydroxylated fatty acids obtained by the present invention have an activity as agonists of nuclear receptors PPARα, PPARγ, and PPARδ, and oxo fatty acids are also considered to have a similar activity. Therefore, these fatty acids can be utilized as metabolism improving agents and the like.

The hydroxylated fatty acids and oxo fatty acids obtained in the present invention can be used by being blended with, for example, pharmaceutical composition, food, or cosmetic based on the conventionally known physiological activity. Therefore, in another embodiment of the present invention, a fatty acid-containing material containing the hydroxylated fatty acids and/or oxo fatty acids obtained in the present invention (e.g., fatty acid-containing composition) is provided. Examples of the aforementioned fatty acid-containing material include the aforementioned pharmaceutical composition, food, cosmetic, feed, additives thereto, and the like.

Examples of the dosage form of a pharmaceutical composition containing hydroxylated fatty acids and oxo fatty acids include powder, granules, pill, soft capsules, hard capsules, tablets, chewable tablets, rapid-disintegrating tablets, syrup, liquid, suspension, suppositories, ointment, cream, gel, adhesives, inhalants, injections, and the like. When they are poorly soluble in water, they are dissolved in a non-hydrophilic organic solvent such as plant-derived oil, animal-derived oil, and the like or are dispersed and emulsified in an aqueous solution together with an emulsifier, a dispersing agent, a surfactant, and the like by a homogenizer (high-pressure homogenizer), and they are used.

Examples of the additives that can be used for formulation include animal and plant oils such as soybean oil, safflower oil, olive oil, germ oil, sunflower oil, beef fat, sardine oil, and the like, polyvalent alcohols such as polyethylene glycol, propylene glycol, glycerol, sorbitol, and the like, surfactants such as sorbitan ester of fatty acids, sucrose fatty acid ester, glycerin fatty acid ester, polyglycerin fatty acid ester, and the like, excipients such as purified water, lactose, starch, crystalline cellulose, D-mannitol, lecithin, gum arabic, sorbitol solution, carbohydrate solution, and the like, sweetener, colorant, pH adjuster, flavoring agents, and the like. A liquid preparation may be dissolved or suspended in water or other suitable media when in use. Also, tablets and granules may be coated by a well-known method.

For administration in the form of an injection, intravenous, intraperitoneal, intramuscular, subcutaneous, transdermal, intraarticular, intrasynovial, intrathecal, intraperiosteum, sublingual, oral administration, and the like are preferable, and intravenous administration or intraperitoneal administration is particularly preferable. The intravenous administration may be any of drip administration and bolus administration.

Examples of the form of the "food" containing hydroxylated fatty acids and oxo fatty acids obtained by the present invention include supplements (powder, granules, soft capsules, hard capsules, tablets, chewable tablets, rapid-disintegrating tablets, syrup, liquid, etc.), drinks (tea, carbonated drink, lactic acid drink, sports drink, etc.), confectionery (gummy candies, jellies, gum, chocolate, cookies, candy, etc.), oil, fat and oil food (mayonnaise, dressing, butter, cream, margarine, etc.), and the like.

The above-mentioned foods can contain, where necessary, various nutrients, various vitamins (vitamin A, vitamin B1, vitamin B2, vitamin B6, vitamin C, vitamin D, vitamin E, vitamin K, etc.), various minerals (magnesium, zinc, iron, sodium, potassium, selenium, etc.), dietary fibers, dispersing agents, stabilizers such as emulsifier and the like, sweetener, flavor components (citric acid, malic acid, etc.), flavoring agents, royal jelly, propolis, *Agaricus*, and the like.

Examples of the "cosmetic" containing hydroxylated fatty acids and oxo fatty acids obtained by the present invention include cream, skin milk, lotion, microemulsion essence, bath powder, and the like, which may be mixed with a flavoring agent and the like.

The present invention is explained in more detail in the following Examples. The Examples are mere exemplifications of the present invention and do not limit the scope of the present invention in any manner.

Example 1

Expression of FA-HYcx1 in *Escherichia coli*

A host vector system consisting of *Escherichia coli* expression vector pET21b (Novagen) and Rosetta 2 (DE3) strains was used. FA-HYcx1 gene segment of SEQ ID NO: 1 was inserted into pET21b to construct an expression vector (pFA-HYcx1). A Rosetta 2 (DE3) strain was transformed with pFA-HYcx1 to give a transformed Rosetta/pFA-HYcx1 strain. The obtained Rosetta/pFA-HYcx1 strain was aerobically cultured in 1 l LB medium (medium containing 1% Bacto Tripton (Difco), 0.5% yeast extract, and 1% sodium chloride (pH 7.0)) containing 0.1 g ampicillin and 0.034 g chloramphenicol at 37° C., 110 rpm. When OD600 nm became 0.5, 500 µl of 1 M IPTG was added, and the cells were further cultured at 18° C. for 21.5 hr. After culture, the mixture was centrifuged at 8,500 rpm for 10 min to give wet cells of the Rosetta/pFA-HYcx1 strain.

Example 2

Production of Hydroxylated Fatty Acids from Unsaturated Fatty Acids by Using Transformed *Escherichia coli* Expressing FA-HYcx1

Using transformed *Escherichia coli* inducing the fatty acid hydration enzyme (FA-HYcx1), a production test of hydroxylated fatty acids from various unsaturated fatty acids was performed. The reaction mixture was 100 mM potassium phosphate buffer (pH 6.5) containing transformed *Escherichia coli* inducing the fatty acid hydration enzyme (wet cell weight 0.3 g/ml), NADH (5 mM), FAD (0.1 mM), an unsaturated fatty acid (10 mM), and BSA (0.3 mg), and the total amount thereof was 1 ml. The reaction was performed by anaerobically shaking at 37° C., 120 rpm for 16-60 hr in the presence of an oxygen adsorbent Anaeropack (Mitsubishi Chemical Corporation). After the reaction, 2 ml of chloroform, 2 ml of methanol, 1 ml of 1.5% KCl were added to the reaction mixture (1 ml), the mixture was stirred, and the chloroform layer was collected. The collected chloroform layer was concentrated by a centrifugal evaporator, and a reaction product and an unreacted substrate were extracted. A part of the extract was subjected to methylesterification and the reaction product was evaluated by gas chromatography.

Example 3

Purification of a Resultant Product from Extract (a Mixture Containing a Substrate and a Resultant Product (a Hydroxylated Fatty Acid)) Obtained in Example 2

The extract (a mixture containing a substrate and a resultant product (a hydroxylated fatty acid)) obtained in Example 2 was subjected to moderate-pressure chromatography, and the solution eluted from the column and divided into fractions was collected. Each collected fraction was analyzed by LC/MS and gas chromatography, and the fractions containing only the resultant product (a hydroxylated fatty acid) were collected and concentrated by rotary evaporator. A part of the obtained final resultant product (a hydroxylated fatty acid) was methylesterified, and the purity of the resultant product was evaluated by gas chromatography. As a result, a resultant product with a purity of not less than 98% was obtained from each substrate. The chemical structure of the resultant product was determined using NMR, 2-dimensional NMR, GC-MS analysis, and the like. As a result, 11-hydroxy-cis-4,cis-7,cis-13,cis-16,cis-19-docosapentaenoic acid with a purity of not less than 98% could be obtained from docosahexaenoic acid. 11-Hydroxy-cis-7,cis-13,cis-16,cis-19-docosatetraenoic acid with a purity of not less than 98% could be obtained from docosapentaenoic acid. 12-Hydroxy-cis-5,cis-8,cis-14,cis-17-eicosatetraenoic acid with a purity of not less than 98% could be obtained from eicosapentaenoic acid. 12-Hydroxy-cis-8,cis-14-eicosadienoic acid with a purity of not less than 98% could be obtained from dihomo-γ-linolenic acid. 12-Hydroxy-cis-5,cis-8-eicosadienoic acid with a purity of not less than 98% could be obtained from mead acid. 12-Hydroxy-cis-8,cis-14,cis-17-eicosatrienoic acid with a purity of not less than 98% could be obtained from eicosatetraenoic acid. 12-Hydroxy-cis-14,cis-17-eicosadienoic acid with a purity of not less than 98% could be obtained from eicosatrienoic acid. 10-Hydroxy-cis-12-octadecenoic acid with a purity of not less than 98% could be obtained from linoleic acid. 10-Hydroxy-cis-12,cis-15-octadecadienoic acid with a purity of not less than 98% could be obtained from α-linolenic acid. 10-Hydroxy-cis-6,cis-12-octadecadienoic acid with a purity of not less than 98% could be obtained from γ-linolenic acid. 10-Hydroxyoctadecanoic acid with a purity of not less than 98% could be obtained from oleic acid. 12-Hydroxy-cis-5,cis-8,cis-14-eicosatrienoic acid with a purity of not less than 98% could be obtained from arachidonic acid.

Example 4

Production of an Oxo Fatty Acid from a Hydroxylated Fatty Acid by Using Anhydrous Chromic Acid ($CrO_3$)

To anhydrous chromic acid (2.67 g) were added sulfuric acid (2.3 ml) and water (7.7 ml), and acetone (90 ml) was added thereto to give a chromic acid solution. 2 g of a hydroxylated fatty acid and 40 ml of acetone were added into an Erlenmeyer flask, and the above-mentioned chromic acid solution was added drop by drop on ice while stirring the mixture with a stirrer. When the solution turned from blue to the color of powdered green tea, the dropwise addition of the chromic acid solution was stopped and the reaction was quenched with isopropyl alcohol. The precipitated sediment was filtered with filter paper and placed in a separating funnel. Diethyl ether (150 ml) and Milli Q water (300 ml) were further added and the mixture was shaken well. The diethyl ether layer was washed several times with Milli Q water. To the diethyl ether layer after washing was added an appropriate amount of sodium sulfate (anhydrous), the mixture was stirred, and the residual water was removed. The anhydrous sodium sulfate added was filtered out with filter paper, the obtained diethyl ether layer was concentrated in rotary evaporator, and the reaction product (an oxo fatty acid) and an unreacted substrate were extracted.

Example 5

Purification of a Resultant Product from Extract (a Mixture Containing a Substrate and a Resultant Product (an Oxo Fatty Acid)) Obtained in Example 4

The extract (a mixture containing a substrate and a resultant product (an oxo fatty acid)) obtained in Example 4 was subjected to moderate-pressure chromatography, and the solution eluted from the column and divided into fractions was collected. Each collected fraction was analyzed by LC/MS and gas chromatography, and the fractions containing only an oxo fatty acid were collected and concentrated by rotary evaporator. A part of the obtained final resultant product was methylesterified, and the purity of the oxo fatty acid was evaluated by gas chromatography. As a result, an oxo fatty acid with a purity of not less than 98% can be obtained from each substrate. The chemical structure of the resultant product was determined using NMR, 2-dimensional NMR, GC-MS analysis, and the like. As a result, 11-oxo-cis-4,cis-7,cis-13,cis-16,cis-19-docosapentaenoic acid with a purity of not less than 98% could be obtained from 11-hydroxy-cis-4,cis-7,cis-13,cis-16,cis-19-docosapentaenoic acid. 11-Oxo-cis-7,cis-13,cis-16,cis-19-docosatetraenoic acid with a purity of not less than 98% could be obtained from 11-hydroxy-cis-7,cis-13,cis-16,cis-19-docosatetraenoic acid. 12-Oxo-cis-5,cis-8,cis-14,cis-17-eicosatraenoic acid with a purity of not less than 98% could be obtained from 12-hydroxy-cis-5,cis-8,cis-14,cis-17-eicosatetraenoic acid. 12-Oxo-cis-8,cis-14-eicosadienoic acid with a purity of not less than 98% could be obtained from 12-hydroxy-cis-8,cis-14-eicosadienoic acid. 12-Oxo-cis-5,cis-8-eicosadienoic acid with a purity of not less than 98% could be obtained from 12-hydroxy-cis-5,cis-8-eicosadienoic acid. 12-Oxo-cis-8,cis-14,cis-17-eicosatrienoic acid with a purity of not less than 98% could be obtained from 12-hydroxy-cis-8,cis-14,cis-17-eicosatrienoic acid. 12-Oxo-cis-14,cis-17-eicosadienoic acid with a purity of not less than 98% could be obtained from 12-hydroxy-cis-14,cis-17-eicosadienoic acid. 10-Oxo-cis-12-octadecenoic acid with a purity of not less than 98% could be obtained from 10-hydroxy-cis-12-octadecenoic acid. 10-Oxo-cis-12,cis-15-octadecadienoic acid with a purity of not less than 98% could be obtained from 10-hydroxy-cis-12,cis-15-octadecadienoic acid. 10-Oxo-cis-6,cis-12-octadecadienoic acid with a purity of not less than 98% could be obtained from 10-hydroxy-cis-6,cis-12-octadecadienoic acid. 10-Oxooctadecanoic acid with a purity of not less than 98% could be obtained from 10-hydroxyoctadecanoic acid. 12-Oxo-cis-5,cis-8,cis-14-eicosatrienoic acid with a purity of not less than 98% could be obtained from 12-hydroxy-cis-5,cis-8,cis-14-eicosatrienoic acid.

Example 6

Measurement of Activity as Agonist of Nuclear Receptors PPARα, PPARγ, and PPARδ

The PPARα, γ, and δ activation ability of the PPAR ligand agents of the present invention was measured in reference to Nobuyuki Takahashi et al., FEBS Letters 514 (2002) p. 315-322, "Dual action of isoprenols from herbal medicines on both PPARgamma and PPARalpha in 3T3-L1 adipocytes and HepG2 hepatocytes.", the section of Materials and Methods "Reporter plasmids and luciferase assays". Specifically, the PPARα, γ, and δ ligand activities were measured by a reporter assay in which binding to a fusion protein of a PPAR ligand binding region and a GAL4 DNA binding region and target gene activation were evaluated by luciferase expression. To be specific, a plasmid containing DNA encoding a fusion protein of a PPARα, γ, or δ ligand binding region and a GAL4 DNA binding region, and a reporter plasmid containing GAL4 binding DNA sequence linked to luciferase were introduced into CV-1 cell. The ligand described below was added to the cells, and after incubation luciferase activity was detected.

The concentration of the sample was adjusted with ethanol. As the negative control, ethanol (0.1%) was used. Each fatty acid was added at 10 μM.

The PPARα, γ, and δ ligand activity data of hydroxylated fatty acids of the present invention are shown in FIG. 1 where representative hydroxylated fatty acids are 11-hydroxy-cis-4,cis-7,cis-13,cis-16,cis-19-docosapentaenoic acid (indicated as "11(OH)DHA") and 12-hydroxy-cis-5,cis-8,cis-14,cis-17-eicosatetraenoic acid (indicated as "12(OH)EPA"), and where other fatty acids for comparison are docosahexaenoic acid (indicated as "DHA"), 14-hydroxy-cis-4,cis-7,cis-10,cis-16,cis-19-docosapentaenoic acid (indicated as "14(OH)DHA"), and eicosapentaenoic acid (indicated as "EPA"). Among them, rare fatty acids of "11(OH)DHA" and "12(OH)EPA" are novel fatty acids. In this Example, "DHA" and "EPA" used were purchased reagents, and "14(OH)DHA" was produced according to the method described in WO 2015/111699.

While the present invention has been described with emphasis on preferred embodiments, it is obvious to those skilled in the art that the preferred embodiments can be modified.

The contents disclosed in any publication cited herein, including patents and patent applications, are hereby incorporated in their entireties by reference, to the extent that they have been disclosed herein.

INDUSTRIAL APPLICABILITY

According to the method of the present invention, since various hydroxylated fatty acids and various oxo fatty acids can be produced, the hydroxylated fatty acids and the oxo fatty acids can be applied to various fields such as medicament, food, and the like. According to the method of the present invention, moreover, novel rare fatty acids can be produced, which is extremely useful.

This application is based on a patent application No. 2019-067966 filed in Japan (filing date: Mar. 29, 2019), the contents of which are incorporated in full herein.

The invention claimed is:

1. A hydroxylated or oxo fatty acid selected from the group consisting of 11-hydroxy-cis-4,cis-7,cis-13,cis-16,cis-19-docosapentaenoic acid, 11-hydroxy-cis-7,cis-13,cis16,cis-19-docosatetraenoic acid, 12-hydroxycis-5,cis-8,cis-14,cis-17-eicosatetraenoic acid, 11-oxo-cis-4, cis-7,cis-13,cis-16,cis-19-docosapentaenoic acid, 11-oxo-cis-7,cis-13,cis-16,cis-19-docosatetraenoic acid, and 12-oxo-cis5,cis-8,cis-14,cis-17-eicosatetraenoic acid.

2. A fatty acid-containing material comprising the hydroxylated or oxo fatty acid according to claim 1 and one or more additives.

3. A fatty acid-containing material comprising the hydroxylated or oxo fatty acid according to claim 1 blended with a pharmaceutical composition, a food or food additive, a cosmetic or cosmetic additive, or a feed or feed additive.

4. The hydroxylated or oxo fatty acid of claim 1 that is 11-hydroxy-cis-4,cis-7,cis-13,cis-16,cis-19-docosapentaenoic acid.

5. The hydroxylated or oxo fatty acid of claim 1 that is 11-hydroxy-cis-7, cis-13,cis16,cis-19-docosatetraenoic acid.

6. The hydroxylated or oxo fatty acid of claim 1 that is 12-hydroxycis-5, cis-8, cis-14,cis-17-eicosatetraenoic acid.

7. The hydroxylated or oxo fatty acid of claim 1 that is 11-oxo-cis-4,cis-7,cis-13,cis-16,cis-19-docosapentaenoic acid.

8. The hydroxylated or oxo fatty acid of claim 1 that is 11-oxo-cis-7,cis-13,cis-16,cis-19-docosatetraenoic acid.

9. The hydroxylated or oxo fatty acid of claim 1 that is 12-oxo-cis5,cis-8,cis-14,cis-17-eicosatetraenoic acid.

* * * * *